United States Patent
McPherson et al.

(10) Patent No.: US 7,598,696 B2
(45) Date of Patent: Oct. 6, 2009

(54) SURGICAL APPARATUS INCLUDING A HAND-ACTIVATED, CONTROL ASSEMBLY AND METHOD OF USING SAME

(75) Inventors: Cameron McPherson, Frisco, TX (US); Rex W. Shores, Norfolk, MA (US); Mitchell Sherry, Fort Worth, TX (US)

(73) Assignee: Medtronic, Inc., Minneapolis, MN (US)

( * ) Notice: Subject to any disclaimer, the term of this patent is extended or adjusted under 35 U.S.C. 154(b) by 1137 days.

(21) Appl. No.: 10/931,102

(22) Filed: Aug. 31, 2004

(65) Prior Publication Data

US 2006/0047272 A1    Mar. 2, 2006

(51) Int. Cl.
*G05B 19/416* (2006.01)
(52) U.S. Cl. .................................. 318/568.18; 318/461
(58) Field of Classification Search .................. 318/567, 318/568.18, 568.21, 461
See application file for complete search history.

(56) References Cited

U.S. PATENT DOCUMENTS

| | | | |
|---|---|---|---|
| 4,835,509 A | 5/1989 | Yoshino et al. | |
| 5,136,220 A | 8/1992 | Philipp | |
| 5,365,155 A | 11/1994 | Zimmermann | |
| 5,712,543 A | 1/1998 | Sjostrom | |
| 5,867,082 A | 2/1999 | Van Zeeland | |
| 5,876,325 A * | 3/1999 | Mizuno et al. | 600/102 |
| 6,017,354 A | 1/2000 | Culp et al. | |
| 6,036,695 A * | 3/2000 | Smith | 606/79 |
| 6,329,778 B1 * | 12/2001 | Culp et al. | 318/434 |
| 6,520,976 B1 | 2/2003 | Gage | |
| 2002/0049464 A1 * | 4/2002 | Donofrio et al. | 606/169 |
| 2002/0087179 A1 | 7/2002 | Culp et al. | |

FOREIGN PATENT DOCUMENTS

| | | |
|---|---|---|
| DE | 2820437 | 7/1979 |
| JP | 2002345843 | 12/2002 |
| WO | WO 99/20187 | 3/1999 |
| WO | WO 03/079911 | 10/2003 |

OTHER PUBLICATIONS

"Midas Rex Legend Gold Touch", Medtronic Powered Surgical Solutions, Version C3.01, Medtronic, Inc. 2004, www.Medtronic.com/neuro/midasrex/goldtouchweb.html.
"Midas Rex Legend High Speed Pneumatic System, Legend Pneumatic Control", Medtronic Powered Surgical Solutions, Version C3.01, Medtronic, Inc. 2004, www.Medtronic.com/neuro/midasrex/pneumaticweb.html.

* cited by examiner

*Primary Examiner*—Rina I Duda
(74) *Attorney, Agent, or Firm*—Haynes and Boone LLP

(57) ABSTRACT

A surgical apparatus and method according to which an assembly is connected to a handpiece and includes a sensing element and a member adapted to move relative to the sensing element to control the operation of a motor in the handpiece.

22 Claims, 2 Drawing Sheets

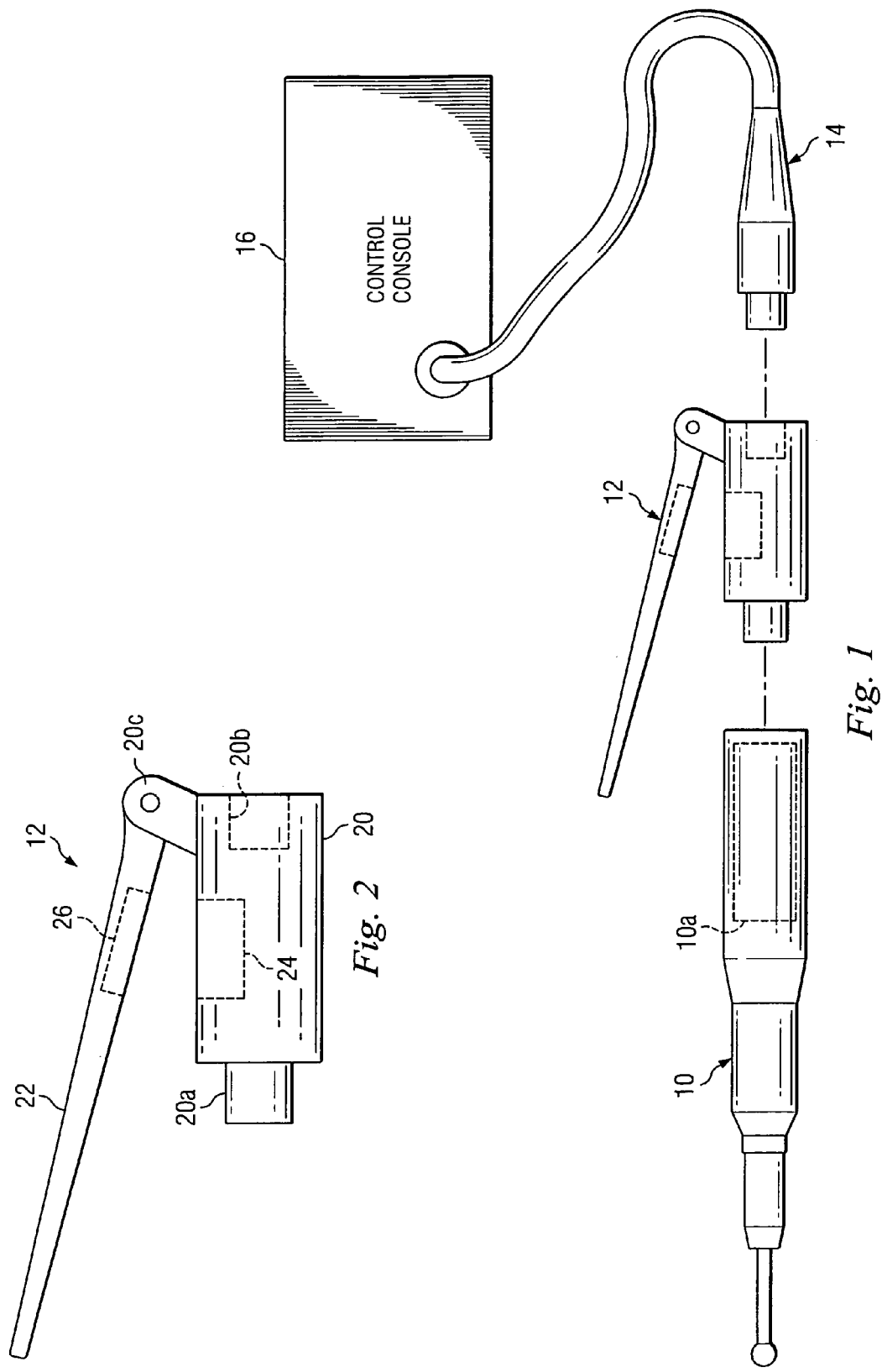

SURGICAL APPARATUS INCLUDING A HAND-ACTIVATED, CONTROL ASSEMBLY AND METHOD OF USING SAME

FIELD OF THE INVENTION

This invention relates to a surgical apparatus including a hand-activated, control assembly, and to a method of using same.

BACKGROUND

Many tools for use in surgical procedures take the form of a handpiece driven by an electric motor to which a cutting accessory, such as a drill bit, bur, saw blade, reamer, and the like, is attached, for removing or separating sections of body tissue.

A hand-activated control switch is usually provided on the handpiece and a sensing element is provided in the handpiece and cooperates with the switch to generate a signal representative of the position of the switch. The signal is sent to a console that converts the available line voltage into a voltage signal and sends the signal to the motor of the handpiece to power the motor.

However, these types of arrangements are not without limitations. For example, if the sensing element within the handpiece fails prematurely, then hand-activation of the handpiece is not possible until it is repaired. Also, the switch is designed to work with only those handpieces that have a sensing element in the handpiece, and handpieces that do not have an imbedded sensing element cannot be used with a hand-activated control switch. Moreover, if the sensing element is in the form of a Hall-effect sensing element that detects the proximity of a magnet in or on the lever, the sensing element could be inadvertently activated if the handpiece were placed on or near a magnet or a magnetic surface.

All patents listed in Table 1 below are hereby incorporated by reference herein in their respective entities. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the teachings of the present invention.

TABLE 1

| Patent/Publication No. | Patented/Published Date | Inventor |
| --- | --- | --- |
| 2002/0087179 A1 | Jul. 4, 2002 | Culp, et al. |

SUMMARY

In order to overcome the above problems, and according to an embodiment of the present invention, a surgical apparatus is provided that includes a sensing element and a switch incorporated in a separate, stand-alone, assembly that connects to a hand piece and to a console. Thus, the assembly can be used with a variety of handpieces, and, if the sensing element fails prematurely, the handpiece is not rendered inoperable, but rather the assembly can simply be replaced with a new one. Also, a Hall-effect sensing element can be used without running the risk of inadvertently activating the sensing element if the handpiece were placed on or near a magnet or a magnetic surface.

Various embodiments of the invention discussed below may possess one or more of the above features and advantages, or provide one or more solutions to the above problems.

BRIEF DESCRIPTION OF THE DRAWINGS

FIG. 1 is an exploded isometric view of an embodiment of the present invention.

FIG. 2 is an enlarged elevational view of a component of the embodiment of FIG. 1.

DETAILED DESCRIPTION

Figure 3:
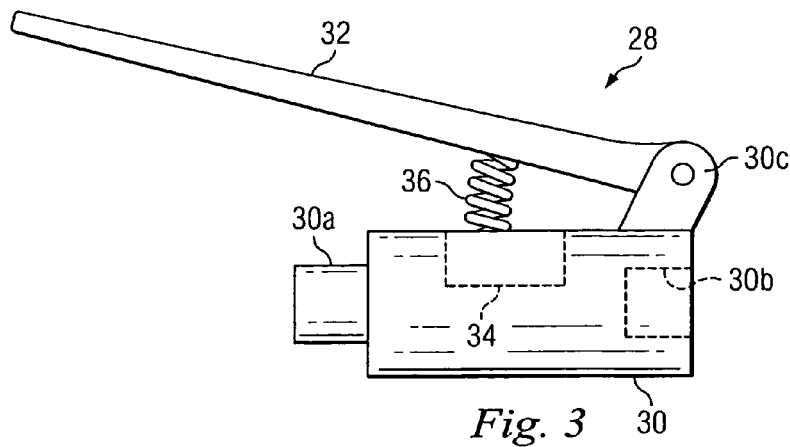
FIGS. 3-5 are views similar to that of FIG. 2 but depicting alternate embodiments of the component of FIG. 2.

Referring to FIG. 1 of the drawings, the reference 10 refers, in general, to a handpiece in the form of a tool for use in surgical procedures. The handpiece 10 is driven by an internal motor 10a, and is adapted to receive a cutting accessory, such as a drill bit, a bur, a saw blade, a reamer, or the like, that can be removably connected to the output shaft of the motor 10a. When the motor 10a is activated in a manner to be described, the output shaft and therefore the cutting accessory are rotated at a predetermined speed for removing or separating sections of body tissue.

A sensing element/switch assembly 12 is electrically and mechanically connected to one end of the handpiece 10 for the purpose of activating the handpiece. An electrical cable 14 is electrically and mechanically connected between the assembly 12 and a console 16 that contains electrical circuitry that converts the available line voltage into a drive signal suitable for driving the motor 10a.

The assembly 12, when manually actuated under conditions to be described, produces signals that are transmitted, via the cable assembly 14, to the console 16 via the cable assembly 14. The console 16 responds to these signals and, in turn, produces the above drive signals that are transmitted to the motor 10a, via the cable assembly 14, so as to cause the motor to operate in a manner to be described.

The assembly 12 is shown in detail in FIG. 2 and includes a housing 20 having a male electrical plug, or jack, 20a extending from one end thereof that mechanically and electrically engages a corresponding female socket (not shown) provided in the corresponding end of the handpiece 10 (FIG. 1). A female socket 20b is formed in the other end of the housing 20 for receiving a corresponding plug, or jack, 14a on the corresponding end of the cable assembly 14. These connections enable signals from the assembly 12 to pass to the console 16 via the cable assembly 14, and signals from the console 16 to pass to the handpiece 10 through the housing 20 and, since they are conventional, they will not be described in any further detail.

A lever 22 is pivotally mounted between two spaced mounting flanges extending from the housing 20, with one of the flanges being referred to by the reference numeral 20c. It is understood that a biasing member (not shown), such as a leaf spring or the like, can be provided that biases the lever in a direction away from the housing 20 and provides resistance to movement towards the housing, in a conventional manner.

A Hall-effect sensing element 24 is disposed in the housing 20 with the upper surface of the sensing element extending flush with the upper surface of the housing, as viewed in FIG. 2. A magnet 26 is provided in the lever 22 in alignment with the sensing element 24, with the lower surface of the magnet extending flush with the lower surface of the lever. The sensing element 24 is conventional and, as such, responds to movement of the lever 22, and therefore the magnet 26, proximate to the sensing element, and outputs a corresponding signal, as will be described in detail. When the lever 22 is released, the above-mentioned leaf spring forces it back to its original position.

The cable assembly 14 (FIG. 1) contains a plurality of electrical conductors (not shown) that electrically connect the sensing element 24 to the console 16, and the console to the motor 10*a*, via the housing 20. Thus, a signal emitted by the sensing element 24 is transmitted to the console 16, causing a drive signal to be transmitted from the console to the motor 10*a* to drive the motor 10*a*. Preferably the latter signal is in the form of a DC voltage that can vary, depending on the position of the magnet relative to the sensing element, to enable the speed of the motor 10*a* to be varied accordingly.

In operation, the surgeon attaches a cutting tool to the handpiece 10 and when ready, manually pushes, or forces, the lever 22 towards the housing 20 so that the magnet 26 approaches the sensing element 24. The sensing element 24 is calibrated to output a signal when the magnet 26 gets within a predetermined distance of the sensing element, and the signal is transmitted to the console 16, via the corresponding conductors in the cable assembly 14.

The above-mentioned electrical circuitry in the console 16 responds to the signal received from the assembly 12, and generates a signal that is passed to the motor 10*a*, via the corresponding conductors in the cable assembly 14. The signal drives the motor 10*a* and enables the speed of the motor to be varied, depending on the position of the magnet relative to the sensing element 24, as discussed above.

An alternate embodiment of an assembly is referred to, in general, by the reference numeral 28 in FIG. 3 and includes a housing 30 having a male electrical plug, or jack, 30*a* extending from one end thereof that mechanically and electrically engages a corresponding female socket (not shown) provided in the corresponding end of the handpiece 10 (FIG. 1). A female socket 30*b* is formed in the other end of the housing 30 for receiving a corresponding plug, or jack (not shown) on the corresponding end of the cable assembly 14. These connections electrically connect the assembly 12 to the console 16, and the console to the handpiece 10 through the housing 30 and, since they are conventional, they will not be described in any further detail.

A lever 32 is pivotally mounted between two spaced mounting flanges extending from the housing 30, with one of the flanges being referred to by the reference numeral 30*c*.

A strain gauge 34 is disposed in the housing 30 with the upper surface of the strain gauge extending flush with the upper surface of the housing, as viewed in FIG. 3. The strain gauge 34 is conventional and, as such, is calibrated to respond to a predetermined force exerted on it and to output a corresponding signal, as will be described in detail.

A helical compression spring 36 extends between the latter surface and the upper surface of the strain gauge 34 so as to normally urge the lever away from the housing 30. When the lever 32 is manually pivoted towards the housing 30, it exerts a force on the spring 36, which compresses the spring and, in turn, exerts a force on the strain gauge 34. When the lever 32 is released, the spring forces it back to its original position.

The cable assembly 14 (FIG. 1) contains electrical conductors (not shown) that electrically connect the strain gauge 34 to the console 16, and the console to the motor 10*a* in the handpiece 10, via the housing 30. Thus, a signal emitted by the strain gauge 34 is transmitted to the console 16, causing a signal to be transmitted from the console to the motor 10*a* to drive the motor. Preferably, the latter signal is in the form of a DC voltage that can vary, depending on the force exerted on the strain gauge 34, to enable the speed of the motor 10*a* to be varied accordingly.

In operation, the surgeon attaches a cutting tool to the handpiece 10 and when ready, manually pushes, or forces, the lever 32 towards the housing 30 against the force of the spring 36 so that a corresponding force is exerted on the strain gauge 34. The strain gauge 34 is calibrated to output a signal when the latter force reaches a predetermined value, and the signal is transmitted to the console 16, via the corresponding conductors in the cable assembly 14.

The above-mentioned electrical circuitry in the console 16 responds to the signal received from the assembly 12, and generates a signal that is passed to the motor 10*a*, via the corresponding conductors in the cable assembly 14. The signal drives the motor and enables the speed of the motor to be varied, depending on the force exerted on the strain gauge 34, as discussed above.

Figure 4:
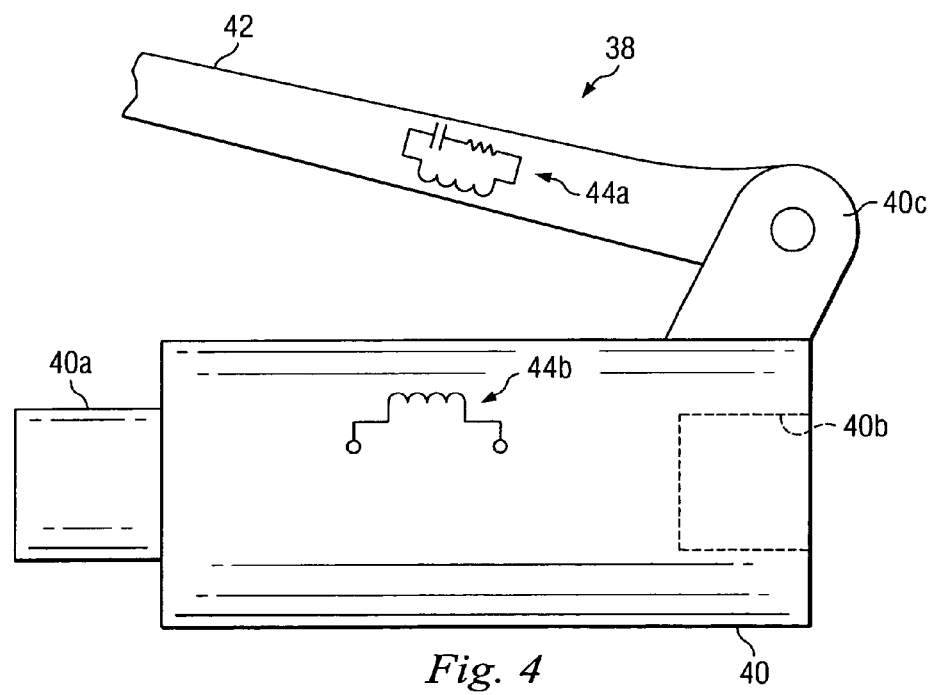

Another alternate embodiment of an assembly is referred to, in general, by the reference numeral 38 in FIG. 4 and includes a housing 40 having a male electrical plug, or jack, 40*a* extending from one end thereof that mechanically and electrically engages a corresponding female socket (not shown) provided in the corresponding end of the handpiece 10 (FIG. 1). A female socket 40*b* is formed in the other end of the housing 40 for receiving a corresponding plug, or jack (not shown) on the corresponding end of the cable assembly 14. These connections electrically connect the assembly 12 to the console 16, and the console to the handpiece 10 through the housing 40 and, since they are conventional, they will not be described in any further detail.

A lever 42 is pivotally mounted between two spaced mounting flanges extending from the housing 40, with one of the flanges being referred to by the reference numeral 40*c*. It is understood that a biasing member (not shown), such as a leaf spring or the like, can be provided that biases the lever 42 in a direction away from the housing 40 and provides resistance to movement towards the housing in a conventional manner.

One portion 44*a* of an inductively coupled circuit is mounted in the lever 42 and another portion 44*b* of the circuit is mounted in the housing 40 and in alignment with the circuit portion 44*a*. The circuit portion 44*a* is in the form of a resonant circuit (RLC) and the circuit portion 44*b* includes an inductor. Thus, the circuit portion 44*a* interacts with the circuit portion 44*b* to induce an output signal voltage in the circuit portion 44*b* when the circuit portion 44*a* is within a predetermined distance of the circuit portion 44*b* as a result of the lever 42 being pivoted towards the housing 40. When the lever 42 is released, the above-mentioned leaf spring forces it back to its original position.

The cable assembly 14 (FIG. 1) contains electrical conductors (not shown) that electrically connect the circuits 44*a* and 44*b* to the console 16, and the console to the motor 10*a* in the handpiece 10, via the housing 40. Thus, a signal emitted by the assembly 38 in the above manner is transmitted to the console 16, causing a signal to be transmitted from the console to the handpiece motor 10*a* to drive the motor. Preferably the latter signal is in the form of a DC voltage that can vary, depending on the relative positions of the circuit portions 44*a* and 44*b*, to enable the speed of the motor 10*a* to be varied accordingly.

In operation, the surgeon attaches a cutting tool to the handpiece 10 and manually pushes, or forces, the lever 42 towards the housing 40. The inductively coupled circuit portions 44*a* and 44*b* are calibrated to output a signal when the lever 42, and therefore the circuit portion 44*a*, gets within a predetermined distance of the circuit portion 44*b* in the housing 40, and the signal is transmitted to the console 16, via the corresponding conductors in the cable assembly 14.

The above-mentioned electrical circuitry in the console 16 responds to the signal received from the assembly 12, and generates a signal that is passed to the motor 10*a*, via the corresponding conductors in the cable assembly 14. The signal drives the motor 10 and enables the speed of the motor to be varied, depending on the relative positions of the circuit portions 44*a* and 44*b*, as discussed above.

Figure 5:
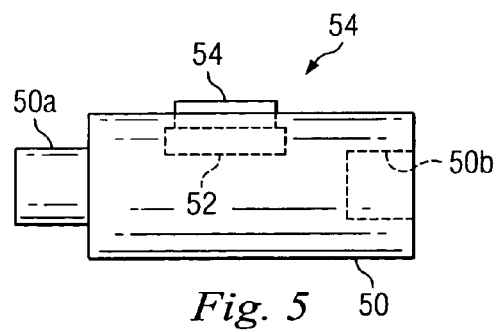

Another alternate embodiment of an assembly is referred to, in general, by the reference numeral 48 in FIG. 5 and includes a housing 50 having a male electrical plug, or jack, 50*a* extending from one end thereof that mechanically and electrically engages a corresponding female socket (not shown) provided in the corresponding end of the handpiece 10 (FIG. 1). A female socket 50*b* is formed in the other end of the housing 50 for receiving a corresponding plug, or jack (not shown) on the corresponding end of the cable assembly 14. These connections electrically connect the assembly 12 to the console 16, and the console to the handpiece 10 through the housing 50 and, since they are conventional, they will not be described in any further detail.

A strain gauge 52 is disposed in an opening in the housing 50 with the upper surface of the strain gauge extending slightly below the upper surface of the housing, as viewed in FIG. 5. The lower portion of a manually-actuatable button 54 also extends in the latter opening over the strain gauge 52, with the lower surface of the button in contact with the upper surface of the strain gauge 52. The upper portion of the button 54 projects outwardly from the upper surface of the housing 50 so that it can be manually engaged, or pressed.

The strain gauge 52 is conventional and, as such, responds to a force exerted on it by a manual pressing of the button 54 downwardly as viewed in the drawing, and is calibrated to output a corresponding output signal. In this context, it is understood that the button 54 is conventional, and, as such, includes a mechanism to return it to its previous position after being pushed downwardly in the above manner.

The cable assembly 14 (FIG. 1) contains electrical conductors (not shown) that electrically connect the strain gauge 52 to the console 16, and the console to the motor 10*a* in the handpiece 10, via the housing 50. Thus, a signal emitted by the assembly 48 in the above manner is transmitted to the console 16, causing a signal to be transmitted from the console to the handpiece motor 10*a* to drive the motor. Preferably the latter signal is in the form of a DC voltage that can vary, depending on the position of the magnet relative to the sensing element, to enable the speed of the motor 10*a* to be varied accordingly.

In operation, the surgeon attaches a cutting tool to the handpiece 10 and manually pushes the button 54 towards the strain gauge 52 to exert a force on the strain gauge 52. The strain gauge 52 is calibrated to output a signal when the latter force reaches a predetermined value, and the signal is transmitted to the console 16, via the corresponding conductors in the cable assembly 14.

The above-mentioned electrical circuitry in the console 16 responds to the signal received from the assembly 12, and generates a drive signal that is passed to the motor 10*a*, via the corresponding conductors in the cable assembly 14. The signal drives the motor 10*a* and enables the speed of the motor to be varied, depending on the amount of force exerted on the strain gauge 52 by the button 54.

Since, in each of the above embodiments the sensing element and switch are both incorporated in a single, separate, stand-alone, assembly that connects to the hand piece and to the console, the assembly can be used with a variety of handpieces. Also, if the sensing element fails prematurely, the handpiece is not rendered inoperable, but rather the sensing element\assembly can simply be replaced with a new one. Further, in the embodiment of FIGS. 1 and 2 there is no risk of inadvertently activating the sensing element if the handpiece were placed on or near a magnet or a magnetic surface.

Variations

It is understood that several variations may be made in the foregoing without departing from the scope of the invention. For example, the sensing element/switch assembly discussed above could be connected directly to the handpiece 10 in manners other than discussed above, such as by mounting or clamping the assembly directly on the handpiece, and electrically connecting the sensing element of the assembly to the console, via the cable assembly 14 described above, or by another cable assembly. Also, the switch in the above embodiments could be replaced by toggle switches, push buttons, or finger/button interfaces. Further, sensing elements other than the ones described above can also be used. Still further, the console can be eliminated if it is not necessary to house the above-described electrical circuit. Moreover, the output shaft of the motor 10*a* can be oscillated, reciprocated, or the like, rather than rotated, as discussed above. Also, the present invention is not limited to surgical instruments employing a cutting element, but may find further applications in which a relatively small instrument is powered from an external console.

The preceding specific embodiments are illustrative of the practice of the invention. It is to be understood that other expedients known to those skilled in the art or disclosed herein, may be employed without departing from the invention or the scope of the appended claims.

In the following claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The invention claimed is:

1. A surgical apparatus comprising:
   a control assembly comprising a housing and a lever pivotally mounted to an external portion of the housing, the housing of the control assembly comprising a first electrical connector adjacent a first end portion and a second electrical connector adjacent a second end portion, the housing further comprising a sensing element for monitoring a relative distance between the lever and the sensing element and emitting a signal representative of the relative distance between the lever and the sensing element;
   a handpiece detachably, electrically coupled to the first electrical connector of the control assembly and detachably, mechanically coupled to the first end portion of the control assembly, the handpiece comprising an electrically operated motor and a surgical tool driven by the electrically operated;
   a cable assembly detachably, electrically coupled to the second electrical connector of the control assembly and detachably, mechanically coupled to the second end portion of the control assembly; and a console electrically coupled with the cable assembly, the console transmitting a drive signal to the electrically operated motor of the handpiece based on the signal representative of the distance between the lever and the sensing element received from the sensing element of the control assembly, the drive signal controlling a speed of the electrically operated motor.

2. The apparatus of claim 1, wherein the first electrical connector and the first end portion of the control assembly together define a male electrical connector and wherein the male electrical connector is detachably mated with a female electrical connector of the handpiece.

3. The apparatus of claim 1, wherein the second electrical connector and the second end portion of the control assembly together define a female electrical connector and wherein the female electrical connector is detachably mated with a male electrical connector of the cable assembly.

4. The apparatus of claim 1, wherein the console comprises an electrical circuit that converts the signal representative of the distance between the lever and the sensing element into a voltage for driving the motor at a speed corresponding to the distance between the lever and the sensing element.

5. The apparatus of claim 4, wherein a decrease in the distance between the lever and the sensing element causes an increase in the voltage for driving the motor at the speed corresponding to the distance between the lever.

6. The apparatus of claim 5, further comprising a biasing member urging the lever away from the sensing element.

7. The apparatus of claim 6, wherein the biasing member comprises a leaf spring.

8. The apparatus of claim 1, wherein the sensing element comprises a hall-effect sensor and wherein the lever further comprises a magnet source.

9. The apparatus of claim 1, wherein the sensing element comprises a strain gauge and wherein the control assembly further comprises a spring extending between the lever and the strain gauge such that movement of the lever towards the strain gauge exerts a force on the strain gauge, and wherein the signal representative of the distance between the lever and the sensing element is based on the force exerted on the strain gauge.

10. The apparatus of claim 1, wherein the sensing element is a first portion of an inductively coupled circuit and wherein the lever comprises a second portion of the inductively coupled circuit.

11. The apparatus of claim 10, wherein the first portion of the inductively coupled circuit comprises an inductor and the second portion of the inductively coupled circuit comprises a resonant circuit.

12. A modular surgical system comprising:
a control assembly comprising a housing and an actuator movably mounted to an external portion of the housing, the housing of the control assembly comprising a first electrical connector adjacent a first end portion and a second electrical connector adjacent a second end portion, the housing further comprising a sensing element for monitoring a relative distance between the actuator and the sensing element and emitting a signal representative of the relative distance between the actuator and the sensing element, the first electrical connector configured to communicate with a plurality of different types of surgical tools comprising an electrically operated motor;
at least one surgical tool detachably, electrically couplable to the first electrical connector of the control assembly and detachably, mechanically couplable to the first end portion of the control assembly, the at least one surgical tool comprising an electrically operated motor and a cutting portion driven by the electrically operated motor;
a cable assembly detachably, electrically couplable to the second electrical connector of the control assembly and detachably, mechanically couplable to the second end portion of the control assembly; and
a console in electrical communication with the cable assembly, the console transmitting a drive signal to the electrically operated motor of the at least one surgical tool based on the signal representative of the relative distance between the actuator and the sensing element received from the sensing element of the control assembly, the drive signal controlling a speed of the electrically operated motor.

13. The system of claim 12, wherein the actuator comprises a lever pivotally attached to the external portion of the housing.

14. The system of claim 12, wherein the actuator comprises a manually-actuatable button.

15. The system of claim 14, wherein the sensing element comprises a load sensor and wherein a portion of the manually-actuatable button is in contact with the load sensor, wherein the load sensor emits the signal representative of the relative distance between the manually-actuatable button and the load sensor based on a force exerted on the load sensor by the manually-actuatable button.

16. The system of claim 12, wherein the sensing element is a first portion of an inductively coupled circuit and wherein the actuator comprises a second portion of the inductively coupled circuit.

17. The system of claim 16, wherein the first portion of the inductively coupled circuit comprises an inductor and the second portion of the inductively coupled circuit comprises a resonant circuit.

18. The system of claim 12, wherein the sensing element comprises a hall-effect sensor and wherein the actuator comprises a magnetic source.

19. A surgical method comprising:
obtaining a control assembly comprising a housing and an actuator movably mounted to an external portion of the housing, the housing of the control assembly comprising a first electrical connector adjacent a first end portion and a second electrical connector adjacent a second end portion, the housing further comprising a sensing element for monitoring a relative distance between the actuator and the sensing element and emitting a signal representative of the relative distance between the actuator and the sensing element, the first electrical connector configured to communicate with a plurality of different types of surgical tools that utilize an electrically operated motor;
electrically and mechanically coupling a first surgical tool to the control assembly such that the first surgical tool is electrically engaged with the first electrical connector, the first surgical tool comprising an electrically operated motor and a cutting portion driven by the electrically operated motor, the first surgical tool electrically and mechanically detachable from the control assembly; and
electrically coupling a console to the second electrical connector of the control assembly via a cable assembly, the console configured to transmit a drive signal to the electrically operated motor of the first surgical tool based on the signal representative of the relative distance between the actuator and the sensing element received from the sensing element of the control assembly, the drive signal controlling a speed of the electrically operated motor.

20. The method of claim 18, further comprising moving the actuator to adjust the speed of the electrically operated motor.

21. The method of claim 18, wherein moving the actuator comprises decreasing the relative distance between the actuator and the sensing element to increase the speed of the electrically operated motor.

22. The method of claim 21, further comprising cutting a tissue with the cutting portion of the surgical tool.

* * * * *